US009113911B2

(12) United States Patent
Sherman

(10) Patent No.: US 9,113,911 B2
(45) Date of Patent: Aug. 25, 2015

(54) ABLATION DEVICE AND METHOD FOR ELECTROPORATING TISSUE CELLS

(75) Inventor: Marshall L. Sherman, Cardiff by the Sea, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 327 days.

(21) Appl. No.: 13/604,700

(22) Filed: Sep. 6, 2012

(65) Prior Publication Data

US 2014/0066913 A1    Mar. 6, 2014

(51) Int. Cl.
*A61B 18/14* (2006.01)
*A61B 18/00* (2006.01)
*A61B 18/02* (2006.01)

(52) U.S. Cl.
CPC ..... *A61B 18/1492* (2013.01); *A61B 2018/0075* (2013.01); *A61B 2018/00214* (2013.01); *A61B 2018/00577* (2013.01); *A61B 2018/00613* (2013.01); *A61B 2018/00994* (2013.01); *A61B 2018/0212* (2013.01); *A61B 2018/1467* (2013.01)

(58) Field of Classification Search
CPC ..................... A61B 18/14; A61B 2018/00577; A61B 18/02; A61B 18/04; A61B 18/1492; A61B 18/15; A61B 18/18; A61B 18/20; A61B 18/24; A61B 2018/00613; A61B 2018/0212
USPC ........ 128/898; 606/41, 48, 50, 10–15, 21, 27, 606/32–34; 607/99
See application file for complete search history.

(56) References Cited

U.S. PATENT DOCUMENTS

| 4,813,934 | A | 3/1989 | Engelson et al. |
| 4,846,174 | A | 7/1989 | Willard et al. |
| 4,968,300 | A | 11/1990 | Moutafis et al. |
| 5,281,213 | A | 1/1994 | Milder et al. |
| 5,397,308 | A | 3/1995 | Ellis et al. |
| 5,398,683 | A | 3/1995 | Edwards et al. |
| 5,423,755 | A | 6/1995 | Kesten et al. |

(Continued)

FOREIGN PATENT DOCUMENTS

| EP | 0896211 A2 | 2/1999 |
| EP | 0957758 B1 | 11/1999 |

(Continued)

OTHER PUBLICATIONS

R. V. Davalos, et al., Tissue Ablation with Irreversible Electroporation, Annals of Biomedical Engineering, vol. 33, No. 2, Feb. 2005 (© 2005) pp. 223-231.

(Continued)

*Primary Examiner* — Christopher A Flory
(74) *Attorney, Agent, or Firm* — Christopher & Weisberg, P.A.

(57) ABSTRACT

A method and system for producing deep lesions without the production of high heat. The method generally includes ablating target tissue cells with a device in communication with an energy generator programmable to ablate tissue using heat energy, electroporation, or a combination thereof. The system generally includes a medical device having a plurality of electrodes at a distal end, and an energy generator in communication with the plurality of electrodes, the generator programmable to deliver alternating current energy between approximately 100 volts RMS and approximately 2000 volts RMS or greater. The generator is further programmable to deliver energy in unipolar mode, bipolar mode, and a combination thereof.

9 Claims, 4 Drawing Sheets

(56) References Cited

U.S. PATENT DOCUMENTS

| | | |
|---|---|---|
| 5,447,497 A | 9/1995 | Sogard et al. |
| 5,472,441 A | 12/1995 | Edwards et al. |
| 5,487,385 A | 1/1996 | Avitall |
| 5,575,766 A | 11/1996 | Swartz et al. |
| 5,584,803 A | 12/1996 | Stevens et al. |
| 5,617,854 A | 4/1997 | Munsif |
| 5,673,695 A | 10/1997 | McGee et al. |
| 5,725,523 A | 3/1998 | Mueller |
| 5,772,681 A | 6/1998 | Leoni |
| 5,776,129 A | 7/1998 | Mersch |
| 5,868,735 A | 2/1999 | Lafontaine |
| 5,910,154 A | 6/1999 | Tsugita et al. |
| 5,928,193 A | 7/1999 | Campbell |
| 5,938,660 A | 8/1999 | Swartz et al. |
| 5,964,778 A | 10/1999 | Fugoso et al. |
| 5,971,979 A | 10/1999 | Joye et al. |
| 5,980,486 A | 11/1999 | Enger |
| 6,012,457 A | 1/2000 | Lesh |
| 6,024,740 A | 2/2000 | Lesh et al. |
| 6,036,697 A | 3/2000 | DiCaprio |
| 6,088,614 A | 7/2000 | Swanson |
| 6,129,724 A | 10/2000 | Fleischman et al. |
| 6,161,543 A | 12/2000 | Cox et al. |
| 6,164,283 A | 12/2000 | Lesh |
| 6,179,810 B1 | 1/2001 | Wantink et al. |
| 6,179,827 B1 | 1/2001 | Davis et al. |
| 6,214,002 B1 | 4/2001 | Fleischman et al. |
| 6,233,491 B1 | 5/2001 | Kordis et al. |
| 6,237,604 B1 | 5/2001 | Burnside et al. |
| 6,241,754 B1 | 6/2001 | Swanson et al. |
| 6,245,064 B1 | 6/2001 | Lesh et al. |
| 6,254,599 B1 | 7/2001 | Lesh et al. |
| 6,283,959 B1 | 9/2001 | Lalonde et al. |
| 6,290,696 B1 | 9/2001 | Lafontaine |
| 6,305,378 B1 | 10/2001 | Lesh |
| 6,312,407 B1 | 11/2001 | Zadno-Azizi et al. |
| 6,325,797 B1 | 12/2001 | Stewart et al. |
| 6,355,029 B1 | 3/2002 | Joye et al. |
| 6,387,092 B1 | 5/2002 | Burnside et al. |
| 6,416,511 B1 | 7/2002 | Lesh et al. |
| 6,428,536 B2 | 8/2002 | Panescu et al. |
| 6,432,102 B2 | 8/2002 | Joye et al. |
| 6,471,694 B1 | 10/2002 | Kudaravalli et al. |
| 6,502,576 B1 | 1/2003 | Lesh |
| 6,514,245 B1 | 2/2003 | Williams et al. |
| 6,514,249 B1 | 2/2003 | Maguire et al. |
| 6,517,514 B1 | 2/2003 | Campbell |
| 6,517,533 B1 | 2/2003 | Swaminathan |
| 6,572,612 B2 | 6/2003 | Stewart et al. |
| 6,575,966 B2 | 6/2003 | Lane et al. |
| 6,578,579 B2 | 6/2003 | Burnside et al. |
| 6,585,733 B2 | 7/2003 | Wellman |
| 6,595,988 B2 | 7/2003 | Wittenberger et al. |
| 6,602,276 B2 | 8/2003 | Dobak, III et al. |
| 6,626,861 B1 | 9/2003 | Hart et al. |
| 6,640,120 B1 | 10/2003 | Swanson et al. |
| 6,641,511 B2 | 11/2003 | Patel et al. |
| 6,645,234 B2 | 11/2003 | Evans et al. |
| 6,648,878 B2 | 11/2003 | Lafontaine |
| 6,648,879 B2 | 11/2003 | Holland et al. |
| 6,648,883 B2 | 11/2003 | Francischelli et al. |
| 6,652,515 B1 | 11/2003 | Maguire et al. |
| 6,659,981 B2 | 12/2003 | Stewart et al. |
| 6,666,858 B2 | 12/2003 | Lafontaine |
| 6,685,732 B2 | 2/2004 | Kramer |
| 6,689,128 B2 | 2/2004 | Sliwa, Jr. et al. |
| 6,702,811 B2 | 3/2004 | Stewart et al. |
| 6,738,673 B2 | 5/2004 | Desai |
| 6,740,104 B1 | 5/2004 | Solar et al. |
| 6,755,822 B2 | 6/2004 | Reu et al. |
| 6,758,847 B2 | 7/2004 | Maguire |
| 6,780,183 B2 | 8/2004 | Jimenez, Jr. et al. |
| 6,811,550 B2 | 11/2004 | Holland et al. |
| 6,837,886 B2 | 1/2005 | Collins et al. |
| 6,875,209 B2 | 4/2005 | Zvuloni et al. |
| 6,893,433 B2 | 5/2005 | Lentz |
| 6,929,639 B2 | 8/2005 | Lafontaine |
| 6,952,615 B2 | 10/2005 | Satake |
| 6,989,009 B2 | 1/2006 | Lafontaine |
| 7,029,470 B2 | 4/2006 | Francischelli et al. |
| 7,097,641 B1 | 8/2006 | Arless et al. |
| 7,097,643 B2 | 8/2006 | Cornelius et al. |
| 7,137,395 B2 | 11/2006 | Fried et al. |
| 7,189,227 B2 | 3/2007 | Lafontaine |
| 7,195,625 B2 | 3/2007 | Lentz |
| 7,226,446 B1 | 6/2007 | Mody et al. |
| 7,465,300 B2 | 12/2008 | Arless et al. |
| 7,479,141 B2 | 1/2009 | Kleen et al. |
| 7,519,410 B2 | 4/2009 | Taimisto et al. |
| 7,540,853 B2 | 6/2009 | Hayzelden |
| 7,655,005 B2 | 2/2010 | Bhola |
| 7,674,256 B2 | 3/2010 | Marrouche et al. |
| 7,706,894 B2 | 4/2010 | Stewart et al. |
| 7,740,627 B2 | 6/2010 | Gammie et al. |
| 2002/0032406 A1 | 3/2002 | Kusleika |
| 2002/0035361 A1 | 3/2002 | Houser et al. |
| 2002/0045894 A1 | 4/2002 | Joye et al. |
| 2002/0087151 A1 | 7/2002 | Mody et al. |
| 2002/0128636 A1 | 9/2002 | Chin et al. |
| 2002/0183691 A1 | 12/2002 | Callister |
| 2002/0188325 A1 | 12/2002 | Hill et al. |
| 2003/0009160 A1 | 1/2003 | Carroll et al. |
| 2003/0125721 A1 | 7/2003 | Yon et al. |
| 2003/0153905 A1 | 8/2003 | Edwards et al. |
| 2003/0158516 A1 | 8/2003 | Wholey et al. |
| 2003/0199861 A1 | 10/2003 | Lafontaine |
| 2004/0034344 A1 | 2/2004 | Ryba |
| 2004/0073203 A1 | 4/2004 | Yu et al. |
| 2004/0073301 A1 | 4/2004 | Donlon et al. |
| 2004/0082947 A1 | 4/2004 | Oral et al. |
| 2004/0158237 A1 | 8/2004 | Abboud et al. |
| 2004/0225342 A1 | 11/2004 | Callister |
| 2005/0020901 A1 | 1/2005 | Belson et al. |
| 2005/0070887 A1 | 3/2005 | Taimisto et al. |
| 2005/0182393 A1 | 8/2005 | Abboud et al. |
| 2005/0182395 A1 | 8/2005 | Lafontaine |
| 2005/0256521 A1 | 11/2005 | Kozel |
| 2005/0261672 A1 | 11/2005 | Deem et al. |
| 2006/0247611 A1 | 11/2006 | Abboud et al. |
| 2006/0271032 A1 | 11/2006 | Chin et al. |
| 2006/0271093 A1 | 11/2006 | Holman et al. |
| 2007/0078453 A1 | 4/2007 | Johnson et al. |
| 2007/0093710 A1 | 4/2007 | Maschke |
| 2007/0203549 A1 | 8/2007 | Demarais et al. |
| 2007/0233222 A1 | 10/2007 | Roeder et al. |
| 2008/0091180 A1 | 4/2008 | Abboud et al. |
| 2008/0103493 A1 | 5/2008 | Abboud et al. |
| 2008/0132885 A1 | 6/2008 | Rubinsky et al. |
| 2008/0200912 A1 | 8/2008 | Long |
| 2008/0281391 A1 | 11/2008 | MacAdam et al. |
| 2009/0228003 A1 | 9/2009 | Sinelnikov |
| 2009/0248012 A1 | 10/2009 | Maor et al. |
| 2009/0248014 A1 | 10/2009 | Shachar et al. |
| 2009/0281477 A1 | 11/2009 | Mikus et al. |
| 2009/0299355 A1 | 12/2009 | Bencini et al. |
| 2009/0306641 A1 | 12/2009 | Govari et al. |
| 2010/0023004 A1 | 1/2010 | Francischelli et al. |
| 2010/0114287 A1 | 5/2010 | Privitera et al. |
| 2010/0137704 A1 | 6/2010 | Vij et al. |
| 2010/0168557 A1 | 7/2010 | Deno et al. |
| 2010/0249771 A1 | 9/2010 | Pearson et al. |
| 2010/0250209 A1 | 9/2010 | Pearson et al. |
| 2010/0261994 A1 | 10/2010 | Davalos et al. |
| 2012/0035601 A1 | 2/2012 | Wittenberger |
| 2012/0071874 A1 | 3/2012 | Davalos et al. |
| 2012/0109118 A1 | 5/2012 | Lalonde et al. |
| 2012/0123411 A1 | 5/2012 | Ibrahim et al. |

FOREIGN PATENT DOCUMENTS

| | | |
|---|---|---|
| EP | 1383426 B1 | 1/2004 |
| WO | 9406349 A1 | 3/1994 |
| WO | 9634571 A1 | 11/1996 |
| WO | 9902096 A1 | 1/1999 |

(56) References Cited

FOREIGN PATENT DOCUMENTS

| WO | 0007657 | A1 | 2/2000 |
|----|---------|----|--------|
| WO | 0042932 | A1 | 7/2000 |
| WO | 0122897 | A1 | 4/2001 |
| WO | 0160441 | A1 | 8/2001 |
| WO | 0207628 | A2 | 1/2002 |
| WO | 02083196 | A3 | 10/2002 |
| WO | 03020334 | A2 | 3/2003 |
| WO | 03026719 | A3 | 4/2003 |
| WO | 03039338 | A2 | 5/2003 |
| WO | 2005067668 | A2 | 7/2005 |
| WO | 2005089853 | A1 | 9/2005 |
| WO | 2006058251 | A2 | 6/2006 |
| WO | 2006118725 | A1 | 11/2006 |
| WO | 2007079438 | A2 | 7/2007 |
| WO | 2008000065 | A1 | 1/2008 |
| WO | 2008142686 | A2 | 11/2008 |
| WO | 2009065042 | A2 | 5/2009 |
| WO | 2009140067 | A1 | 11/2009 |
| WO | 2010002888 | A2 | 1/2010 |
| WO | 2010006229 | A1 | 1/2010 |
| WO | 2010067360 | A2 | 6/2010 |

OTHER PUBLICATIONS

International Search Report and Written Opinion dated Dec. 13, 2013 for International Application Serial No. PCT/US2013/056756, International Filing Date: Aug. 27, 2013 consisting of 10 pages.

ABLATION DEVICE AND METHOD FOR ELECTROPORATING TISSUE CELLS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for high-voltage radiofrequency ablation using combined heat and electroporation to produce a deeper lesion while avoiding the production of excess heat at the tissue surface.

BACKGROUND OF THE INVENTION

The use of an electric field is relatively new medical treatment for such purposes as the enhancement of chemotherapy (electrochemotherapy), cellular ablation, and intracellular electromanipulation. All three treatments involve pulses of energy, although using different frequencies and pulse durations. Ablation, such as of tumor or liver cells, occurs when cells are exposed to high-voltage electrical field pulses. In the presence of these pulses, the electrochemical potential across the cell membrane is altered and instabilities in the polarized lipid bilayer are induced, which may lead to the development of irreversible pores (or enlargement of existing pores) in the cell membrane. The phenomenon may cause cell death through the loss of cellular contents or entry of surrounding contaminants.

This increase in cell membrane permeability when exposed to an electric field is generally referred to as electroporation, and may be brought about by the application of pulses of direct current (DC) electrical energy applied internally (via, for example, a catheter) or externally. However, the repetition frequency of electric pulses is considered to effect muscle contractions, which can produce a burning sensation or intense pain in patients.

Further, deep lesions are sometimes required to effectively treat some cardiac conditions. For example, atrial fibrillation may be caused by aberrant electrical conductivity pathways through and around scarred myocardial tissue, which cause an electrical "feedback loop" and irregular heartbeat. To destroy these aberrant pathways, the myocardial tissue must be ablated deeply enough to stop the problematic electrical signals from continuing. The creation of deep lesions requires prolonged application of energy and/or high temperatures. However, the surface of the tissue must be maintained at cool enough temperatures to avoid charring or micro embolus formation, which can lead to unintended tissue death or stroke.

Therefore, a system and method are desired that is capable of producing deep lesions without the production of high heat and without causing patient discomfort. The system and method of the present invention involve the application of higher voltage radiofrequency energy to use both heat and electroporation to perform ablation while avoiding undesired tissue damage due to excess heat at the tissue surface.

SUMMARY OF THE INVENTION

The present invention advantageously provides a method and system for producing deep lesions without the production of high heat. The method generally includes treating target tissue cells using a medical device that is configured to selectively deliver energy at a voltage at which tissue electroporation occurs, energy at a voltage at which heat ablation occurs, or any voltage therebetween. The medical device may also be configured to reduce the temperature of the tissue cells to a temperature at which cryoablation occurs. The applied energy may be radiofrequency (RF) energy, and the RF energy may be an alternating current energy having a frequency of between approximately 20 kHz and approximately 1 MHz. Electroporation energy may be delivered between approximately 500 volts RMS and approximately 3000 volts RMS. Further, a voltage at which heat ablation occurs is applied to target tissue cells before applying a voltage at which electroporation occurs. Still further, the medical device may include a plurality of electrodes and radiofrequency energy is delivered to each of the plurality of electrodes, the energy delivered to each of the plurality of electrodes being either at in-phase angle or out-of-phase angle relative to the energy delivered to adjacent electrodes.

In an another embodiment, the method may include positioning a medical device in contact with an area of target tissue, the medical device including a plurality of electrodes in communication with a radiofrequency generator, the generator programmable to deliver energy in at least one of bipolar mode and combination of unipolar mode and bipolar mode, delivering to the target tissue both radiofrequency energy from the medical device at between approximately 500 volts RMS to approximately 3000 volts RMS, and delivering alternating current radiofrequency energy from the medical device at between approximately 100 volts RMS to approximately 150 volts RMS to an area of target tissue. The method may further include delivering alternating current radiofrequency energy at a voltage between approximately 150 volts RMS and approximately 500 volts RMS. The energy delivered to each of the plurality of electrodes may be delivered at either an in-phase angle or out-of-phase angle relative to the energy delivered to adjacent electrodes.

The system may generally includes a medical device having a plurality of electrodes at a distal end of the device, and energy generator in communication with the plurality of electrodes, the generator programmable to deliver between approximately 100 volts RMS and approximately 3000 volts RMS. The device may further include one or more sensors at the distal end. The energy generator may be programmable to deliver between approximately 100 volts RMS and approximately 150 volts RMS during a first treatment cycle and between approximately 500 volts RMS and approximately 3000 volts RMS during a second treatment cycle. Further, the energy generator may be programmable to deliver energy to the plurality of electrodes in at least one of unipolar mode, bipolar mode, and combination thereof.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
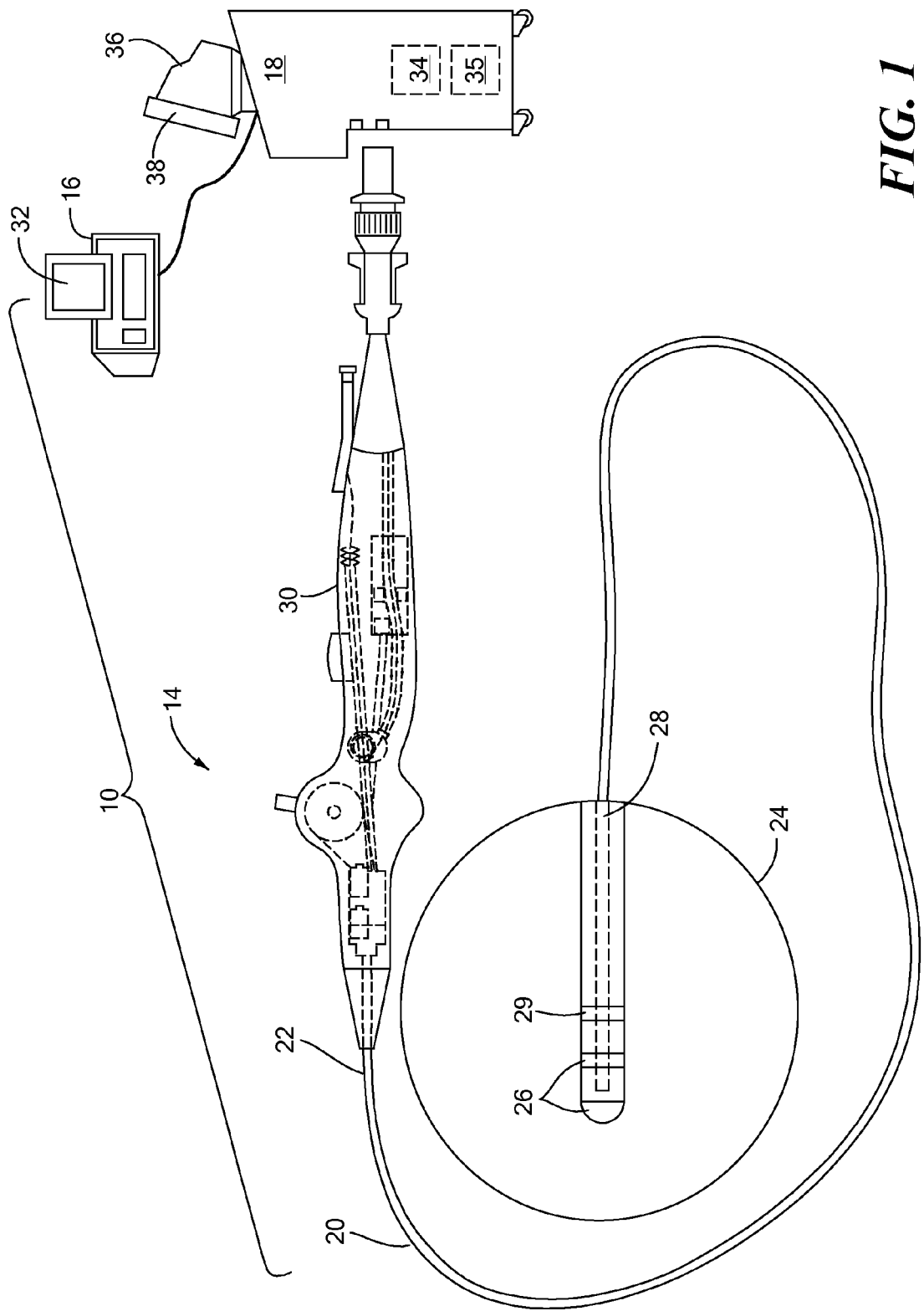
FIG. 1 shows a first embodiment of a system in accordance with the present invention.

The present invention provides systems and methods of use thereof for producing deep lesions without the production of high heat and without causing patient discomfort. High-frequency alternating current (AC) radiofrequency (RF) energy may be used (for example, between approximately 20 kHz and approximately 1 MHz, as this range does not stimulate the heart but still provides an electrophoretic effect) is used to ablate tissue through either cellular electroporation or heat or a combination thereof, while maintaining tissue surface temperatures below a threshold temperature that causes unintentional charring or the formation of micro emboli. Further, this application of AC RF energy does not cause patient discomfort or pain as does the application of DC energy. Still further, the AC RF energy may be applied at a voltage capable of ablating tissue due to heat energy, a voltage capable of ablating tissue due to electroporation effects, or a voltage at any point along a continuum between heat energy and electroporation energy. Referring now to the drawing figures in which like reference designations refer to like elements, FIG. 1 shows a first embodiment of a system 10 for generating and applying high-voltage RF energy to an area of target tissue 12. The system 10 may generally include a medical device 14, an energy generator 16, and a console 18 for operating, monitoring, and regulating the operation of the device 14.

Figure 2:
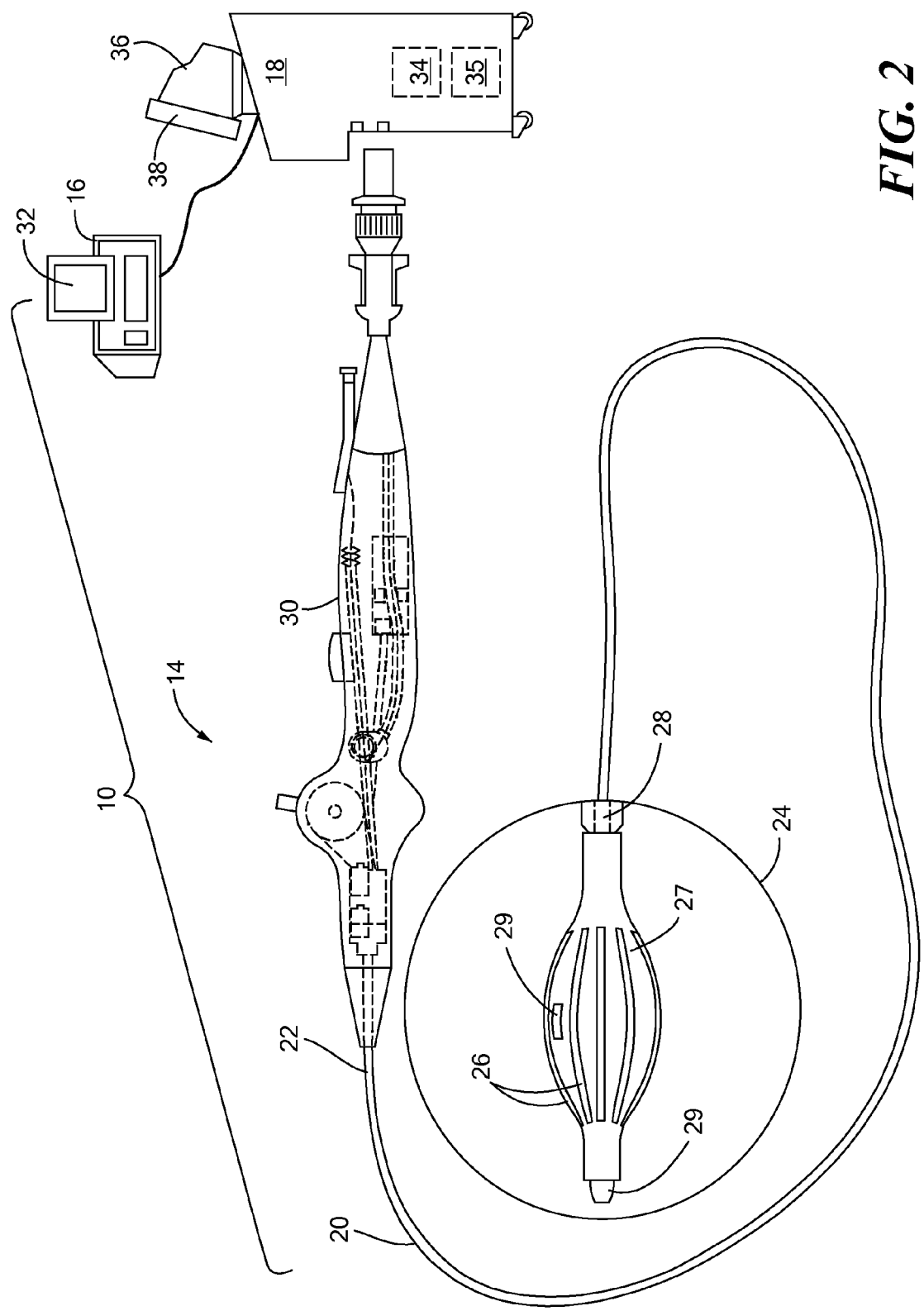
FIG. 2 shows a second embodiment of a system in accordance with the present invention.

Referring to FIGS. 1 and 2, the medical device 14 may be a catheter, for example, an RF ablation catheter as shown in FIG. 1. The catheter 14 may be adapted for use with a single energy modality only (for example, RF energy), or a combination of energy modalities (for example, RF plus laser, microwave, cryoablation, and/or ultrasound energy). Regardless of the number of energy modalities to which the catheter 14 is suited, however, the catheter 14 must at least be capable of transmitting an electric field that will electroporate target tissue cells 12. For example, the catheter 14 may be capable of transmitting RF energy at a voltage of approximately 2000 V or greater. The catheter 14 may include a flexible elongate body 20 having a proximal portion 22 and a distal portion 24. The distal portion 24 of the elongate body 20 may have a fixed diameter (as shown in FIG. 1), or may include an expandable element (as shown in FIG. 2). The elongate body 20 may include a plurality of treatment elements, such as electrodes 26, at the distal portion 24 for delivering energy to target tissue 12. If a secondary energy modality is used in addition to RF energy, the treatment elements may also include a thermally-transmissive region in addition to the plurality of electrodes 26, such as a balloon or other expandable element, metal structure directly or indirectly exposed to a flow path of cryogenic fluid, or one or more thermally-conductive polymers or composites. For example, FIG. 2 shows a catheter 14 having a cryoablation balloon 27 in addition to an electrode array 26. The plurality of electrodes 26 may be of any number, configuration, or shape, for example, a plurality of discrete electrodes, band electrodes that partially or entirely circumscribe the elongate body 20 (as shown in FIG. 1) or balloon 27, longitudinally oriented electrodes (as shown in FIG. 2), a tip electrode (as shown in FIG. 2), or clusters of electrodes. The electrodes may be in the form of conductive strips applied to the outer surface of the distal portion 24, and may be made of metal, conductive polymers, conductive ink printing, or micro-capillary printing. The electrodes 26 may be adhesively bonded to the device 14 or applied by ion-deposition or plasma deposition. Alternatively, conductive materials such as silver, platinum, or gold may be doped or otherwise mixed into the balloon 27 material.

The catheter 14 may define one or more lumens 28 for providing mechanical, electrical, and/or fluid communication between the proximal portion 22 and the distal portion 24 of the elongate body 20. The one or more lumens 28 may be thermally insulated to substantially prevent heat exchange between, for example, a lumen 28 (and any devices or components therein) and the plurality of electrodes 26. The distal portion 24 of the elongate body 20 may further include one or more sensors 29 for detecting pressure, temperature, electrical impedance, or other system and/or environmental parameters (for example, the surface temperature of the target tissue 12). The one or more sensors 29 may be of any configuration (for example, ring sensors as shown in FIG. 1, or tip and balloon sensors as shown in FIG. 2), and may be in communication with the console 18, with which the user may control the energy delivered to the catheter 14. For example, if a temperature sensor 29 detects a tissue 12 surface temperature at or near a threshold temperature, the energy application may be stopped (either automatically by the system 10 or manually by the user) and/or the RF voltage reduced in order to avoid unintended tissue damage.

The proximal portion 22 of the elongate body 20 may be coupled to a handle 30, which may include various ports for electrical and fluid connectors, leads, junctions, or tubes, and may also include various control assemblies, such as switches or valves, as well as safety detection or shutdown components. For example, the handle 30 may include connectors that are matable directly or indirectly by way of one or more umbilicals to the console 18. Further, the handle 30 may also include an element such as a lever or knob for manipulating or deflecting at least a portion of the elongate body 20.

Continuing to refer to FIGS. 1 and 2, the energy generator 16 may be an RF energy generator capable of delivering energy in multiple modes, such as unipolar, bipolar, and combination thereof, such as 4:1, 2:1, and 1:1 (a duty cycle-controlled power delivery system). Further, the generator 16 is capable of delivering pulsed alternating current (AC) RF energy of approximately 500 volts RMS to approximately 2000 volts RMS or more (for example, up to 3000 V). At these higher voltages, the majority of the cell damage would be due to electroporation of the target tissue 12 cells (for example, to a temperature of above 45° C., without a substantial increase in the temperature of the electrodes 26. During electroporation, the RF energy may be delivered in multiple ON/OFF cycles in which the ON cycle only represents approximately 0.5% to approximately 1% of the total duty cycle time. These quick bursts of high-voltage energy create pores in membranes of target tissue cells, but will not damage the tissue with heat. Therefore, deeper lesions may be achieved without a substantial increase in heat energy, and thus unintended damage to non-target tissue or tissue charring may be avoided. For example, the tissue surface temperature may be maintained at a temperature below 45° C., the temperature at which irreversible unintended damage may occur. This, in turn, reduces the likelihood of potentially lethal complications (for example, the formation of micro emboli) and reduces patient discomfort.

The generator 16 may also be capable of operating at a lower voltage (for example, approximately 100 to approximately 150 volts RMS) for ablating tissue using primarily heat energy. To generate heat energy, the RF energy may be delivered in multiple ON/OFF cycles in which the ON cycle is greater than, for example, 2% of the total cycle. Tissue may be irreversibly damaged at temperatures above 45° C.; however, sub-lethal heat energy may be applied to temporarily "stun" (rather than irreversibly damage) an area of target tissue to help determine whether the area of stunned tissue is perpetuating an aberrant electrical signal involved in an arrhythmia, and therefore whether subsequent electroporation of the stunned area of tissue will block the aberrant electrical signal. Because electroporation may not result in immediate ablation of the treated tissue (that is, the treated cells may continue to function somewhat normally for a time after electroporation) and thus immediate current blockage, it may be difficult to determine whether the correct area of tissue was electroporated. Therefore, the combination of heat energy and electroporation may result in more effective and efficient ablation.

The generator 16 may allow for the selection of simultaneous or selective energy delivery across electrode pairs, and may further include a user interface 32 for monitoring ablation time, electrode temperature, time at temperature, and the like. The energy output scheme of the generator 16 may be programmable independently of the console 18 via the user interface 32. Further, the generator 16 may be capable of delivering an adjustable voltage so ablation may be caused using primarily heat (for example, between approximately 100V to approximately 150V), primarily electroporation (for example, between approximately 500V and approximately 2000 V or more), or any combination thereof (a voltage anywhere along the continuum between heat voltage and electroporation voltage). Additionally, the generator 16 may be programmable to manipulate characteristics of the energy output, such as the ON cycle percentage of the total duty cycle, the voltage, and the number of ON/OFF sequences. In a non-limiting example, the voltage could be adjusted to alternately ablate tissue 12 using primarily heat, primarily electroporation, or combination thereof. In an additional non-limiting example, cryoablation may be used in addition to electroporation (as shown in FIG. 2), in which case the generator 16 may maintain voltage at approximately 500 to approximately 2000 volts RMS or more to cause electroporation of cells, which may complement the cryoablation. The cryoablation and RF ablation may be used either simultaneously or alternately. The temperature required for cryoablation may be lower than would normally be required to ablate tissue, thus requiring lower coolant flow rates and/or volume. Still further, a second generator 34 may be used if microwave, laser, or ultrasound energy is also used. Thus, the user may have very precise control over the treatment process.

Continuing to referring to FIGS. 1 and 2, the console 18 may be used to control the temperature of one or more components of the medical device 14 during operation of the system 10. The console 18 may include a power source 35, a computer 36 in communication with other system 10 components (such as the plurality of electrodes 26, one or more sensors 29, and/or generator 16) and having one or more screens or displays 38 with which the user may monitor and/or adjust system 10 parameters. Additionally or alternatively, the computer 36 may be programmed to automatically adjust such parameters as voltage delivered by the generator 16, coolant volume and flow delivered from a coolant source 40 (as shown in FIG. 2), and effective temperature of the one or more treatment elements based at least in part on signals received from the one or more sensors 29. Further, temperature regulation may be achieved through the implementation of one or more active thermal elements coupled to the medical device 14 and/or in communication with the computer 36, such as one or more cooling components (such as subcoolers, Peltier coolers, Joule-Thompson coolers, Stirling engine, or the like) and/or active heat sources (such as heating elements, immersion heaters, circulation heaters, or other devices for warming fluids or gases). If the system 10 is configured for cryoablation, the system 10 may include not only a coolant source 40, but a coolant return reservoir and vacuum pump as well, and the device 14 may include a fluid injection lumen, a fluid return lumen, a fluid injection element, and the like.

Figure 3A:
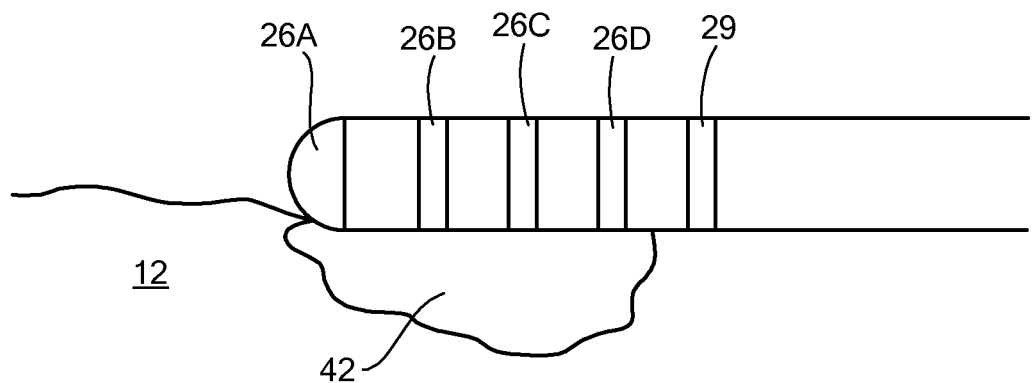
FIGS. 3A and 3B show a distal portion of a medical device having a plurality of electrodes and lesions created when the device is operating in unipolar or bipolar mode.
Figure 3B:
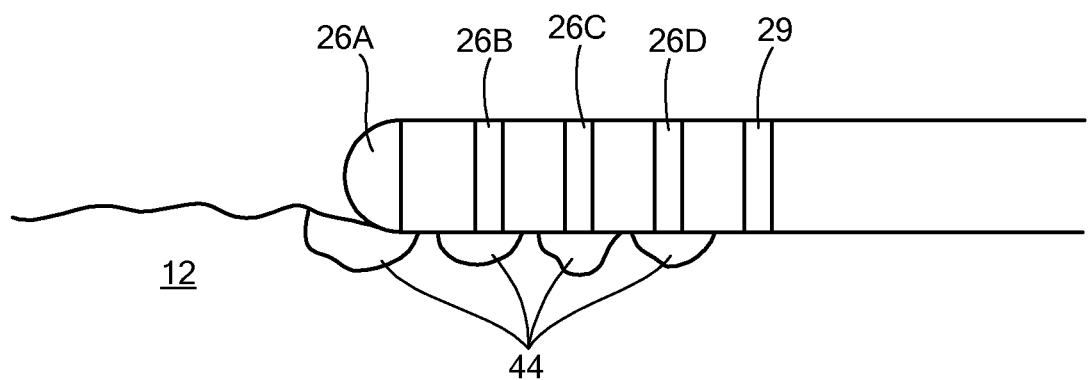

Referring now to FIGS. 3A and 3B, the distal portion 24 of the medical device 14 may include a plurality of electrodes 26, with each electrode being capable of operating out of phase from one or more adjacent electrodes. This allows for the device 14 to operate in unipolar mode, bipolar mode, or combination thereof. Further, this mode selection may be used in conjunction with the voltage selection, thereby making possible a wide variety of treatment effects. As shown in FIGS. 3A and 3B, the distal portion 24 may include four electrodes 26A, 26B, 26C, 26D, although it is understood that any number or configuration of electrodes may be used, such as an array or mesh including a plurality of electrodes.

All four electrodes may be activated to apply energy at 1000 V RMS in bipolar mode (as shown in FIG. 3A). As a non-limiting example, electrode 26A may apply energy at 1000 V at 0°, electrode 26B may apply energy at 1000 V at 180° out of phase from electrode 26A, electrode 26C may apply energy at 1000 V at 0° (same phase as electrode A), and electrode 26D may apply energy at 1000 V at 180° out of phase from electrode 26C. In this case, the energy applied between any two electrodes would be twice the voltage applied by either electrode (e.g., 2000 V RMS). However, using a different phase angle would create a different combined voltage. For example, If electrodes 26A and 26C apply energy at 1000 V at 0° and electrodes 26B and 26D apply energy at 1000 V at 90°, the combined voltage between electrodes 26A and 26B (or any combination of adjacent electrodes) would be approximately 1400 V RMS (or approximately 1.414 times 1000 V). Similarly, a 60° shift would result in a combined voltage between electrodes 26A and 26B (or any combination of adjacent electrodes) of 1000 V (creating no increased effect). In fact, any phase angle between 0° and 180° could be used to create the desired combined voltage between electrodes. Further, the amount of voltage delivered to the target tissue also depends on the distance between electrodes. For example, if electrodes 26A and 26B deliver a combined voltage of 1000 V and the electrodes are spaced 10 mm apart, each mm of tissue between the electrodes would receive 100 V. Alternatively, the electrodes may be activated to apply energy in unipolar mode, with no phase difference between electrodes (as shown in FIG. 3B). Therefore, the multi-electrode device 14 is capable of creating a contiguous lesion 42 when operating in bipolar mode or creating discrete lesions 44 when operating in unipolar mode. Thus, the effective voltage applied to the tissue may be manipulated by phase shift in bipolar mode and voltage delivered to each electrode (in either unipolar mode or bipolar mode), calculated as a function of the distance between electrodes. Further, as discussed above, the device 14 may be used to ablate tissue using either thermal energy, electroporation, or a combination thereof. Still further, the device 14 may be used to ablate using electroporation and another energy modality (such as cryoablation) simultaneously.

Figure 4:
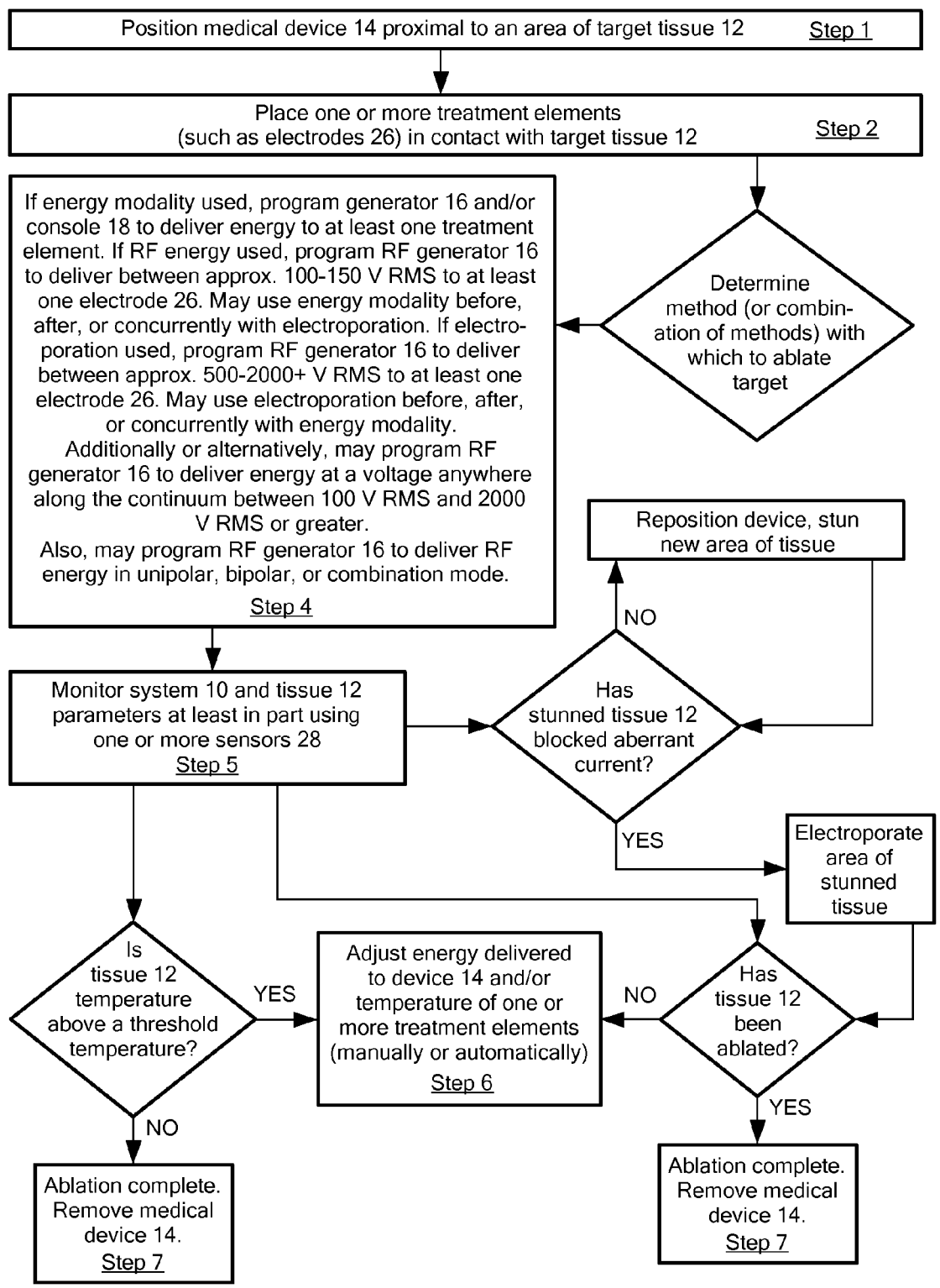
FIG. 4 shows a flow chart of a method in accordance with the present invention.

Referring now to FIG. 4, a flow chart of a method of ablation using electroporation and heat energy is shown. It will be understood that cryoablation is included herein as an "energy modality," even though cryoablation involves the removal of heat from tissue. The method of FIG. 4 generally includes positioning a medical device 14 proximal to an area of target tissue 12, determining the method with which the target tissue 12 will be ablated, activating one or more treatment elements, and adjusting an energy generator as necessary to ablate the target tissue 12. Step 1 includes positioning a medical device 14 proximal to an area of target tissue 12. As non-limiting examples, the target tissue may be cardiac, (such an endocardial or epicardial tissue), liver, pancreatic, renal, or tumor tissue. In fact, the target tissue 12 may be any biological tissue in which electroporation would create pores within the tissue cellular membranes and in which irreversible electroporation would cause cell death.

In Step 2 of FIG. 4, the treatment elements are placed in contact with the target tissue 12. For example, if cryoablation is used in addition RF energy (for electroporation), the balloon 27 and plurality of electrodes 26 should be placed in contact with the target tissue 12. In Step 3, the method with which the target tissue 12 will be ablated is determined. For example, if only electroporation is desired, the generator 16 may be programmed to deliver energy at between approximately 500 and approximately 2000 V or greater (for example, 3000 V; "electroporation voltage") to all of the plurality of electrodes 26. If the user desires to ablate the target tissue 12 using only heat energy or cryoablation, the generator 16 may be programmed to deliver energy at between approximately 100 to approximately 150 volts RMS ("ablation voltage") to all of the plurality of electrodes 26 and/or the flow of coolant initiated. If the user desires to ablate the target tissue 12 using a combination of electroporation and heat energy (and/or cryoablation), the generator may be programmed to deliver energy at a desired voltage anywhere along the continuum between electroporation voltage and heat voltage. This may be accomplished by adjusting the output voltage from the generator 16 or adjusting the phase angle between adjacent electrodes. Or, electroporation voltage to some electrodes 26 and ablation voltage to some electrodes 26. Or, the voltage level output by the plurality of electrodes and/or duration of energy application may be adjusted such that the tissue 12 is ablated by both heat and electroporation. Thus, each activated electrode 26 may receive either electroporation voltage or ablation voltage; some electrodes may not receive voltage at all (that is, may not be activated). Or, each activated electrode 26 may receive a voltage that effects both electroporation and heat ablation. Further, the generator 16 may be programmed to deliver heat voltage followed by electroporation voltage to all electrodes 26, such as when testing an area of tissue with heat energy to determine if electroporation of that tissue will effectively block an aberrant electrical current. Therefore, the generator 16 may be programmed to deliver heat energy, electroporation energy, or any combination thereof to the plurality of electrodes 26 as desired (Steps 4A and 4B). Still further, the generator 16 may be programmed to deliver energy in unipolar mode, bipolar mode, or combination thereof.

In Step 5 of FIG. 4, system 10 and tissue 12 parameters may be monitored. During ablation, one or more sensors 29, such as temperature sensors, may measure the temperature of the tissue surface. If the temperature sensors detect a tissue temperature that is above a threshold temperature (for example, 45° C.), the system 10 may be adjusted manually by the user or the energy generator 16 and/or the computer 36 may be programmed to automatically adjust voltage, coolant flow, effective temperature of treatment elements, and/or other system 10 parameters to ensure unintended tissue damage does not occur (Step 6). Additionally, the medical device 14 may include one or more electrical conductivity sensors, which may provide mapping functionality and/or detect the status of the target tissue 12. For example, based at least in part on electrical conductivity measurements, the user and/or system 10 may determine whether the target tissue 12 has been ablated (Step 6B). If the target tissue 12 has not been satisfactorily ablated, the system 10 may likewise be adjusted manually by the user or the energy generator 16 and/or the computer 36 may be programmed to automatically adjust voltage, coolant flow, operating mode, effective temperature of treatment elements, and/or other system 10 parameters to ensure complete ablation of the target tissue 12 (Step 6).

After completion of Steps 1-6, the target tissue 12 is ablated. In Step 7 of FIG. 4, the catheter 14 may be removed from the area of target tissue 12.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for ablating tissue, comprising:
thermally treating the tissue by transmitting sub-lethal thermal energy using a medical device to stun the tissue, the medical device being in electrical communication with a radiofrequency energy source that provides the sub-lethal thermal energy;
determining whether stunning the tissue with the thermal treatment affected a perpetuation of an aberrant electrical signal within the tissue; and
when it is determined that stunning the tissue with the thermal treatment affects the perpetuation of the aberrant electrical signal within the tissue, non-thermally electroporating the tissue by transmitting high-frequency alternating current radiofrequency energy to the tissue using the medical device, the radio frequency energy source providing the high-frequency alternating current radio frequency energy.

2. The method of claim 1, wherein the high-frequency alternating current radiofrequency energy is delivered at between approximately 500 volts RMS and approximately 3000 volts RMS.

3. The method of claim 1, wherein the medical device includes a plurality of electrodes in electrical communication with the radiofrequency energy source, the radiofrequency energy delivered to each of the plurality of electrodes being either at in-phase angle or out-of-phase angle relative to the energy delivered to adjacent electrodes.

4. The method of claim 3, wherein the radiofrequency energy delivered to each of the plurality of electrodes is at an out-of-phase angle between adjacent electrodes, the phase angle being determined at least in part by the desired voltage to be applied to the target tissue.

5. The method of claim 1, wherein a surface temperature of the target tissue remains below a threshold temperature at which unintended tissue damage occurs during the thermal treatment of the tissue.

6. A method of ablating tissue, comprising:
positioning a medical device in contact with an area of target tissue, the medical device including a plurality of electrodes in communication with a radiofrequency generator, the generator programmable to deliver energy in at least one of bipolar mode and combination of unipolar mode and bipolar mode;
delivering a sub-lethal amount of alternating current radiofrequency energy from the medical device at between approximately 100 volts RMS to approximately 150 volts RMS to an area of target tissue to stun the target tissue;

determining whether stunning the target tissue affects the perpetuation of an aberrant signal within the tissue; and when it is determined that stunning the target tissue affects the perpetuation of an aberrant signal within the tissue, at least one of:

delivering alternating current radiofrequency energy from the medical device at between approximately 500 volts RMS to approximately 3000 volts RMS to an area of target tissue to ablate the target tissue with heat energy; and delivering alternating current radiofrequency energy from the medical device at between approximately 100 volts RMS to approximately 150 volts RMS to the area of target tissue to ablate the target tissue with non-thermal electroporation energy.

7. The method of claim 6, further comprising delivering alternating current radiofrequency energy at a voltage between approximately 150 volts RMS and approximately 500 volts RMS.

8. The method of claim 6, wherein the energy delivered to each of the plurality of electrodes is delivered at either an in-phase angle or out-of-phase angle relative to the energy delivered to adjacent electrodes.

9. The method of claim 8, wherein energy delivered to each of the plurality of electrodes is at an out-of-phase angle between adjacent electrodes, the phase angle being determined at least in part by the desired voltage to be applied to the target tissue.

* * * * *